US011401221B2

(12) United States Patent
Reich et al.

(10) Patent No.: US 11,401,221 B2
(45) Date of Patent: Aug. 2, 2022

(54) METHOD FOR PRODUCING A STREAM OF PROPYLENE AND ASSOCIATED FACILITY

(71) Applicant: TECHNIP FRANCE, Courbevoie (FR)

(72) Inventors: Véronique Reich, Vaucresson (FR); Bruno Destour, Rueil Malmaison (FR)

(73) Assignee: TECHNIP FRANCE, Courbevoie (FR)

( * ) Notice: Subject to any disclaimer, the term of this patent is extended or adjusted under 35 U.S.C. 154(b) by 0 days.

(21) Appl. No.: 17/057,660

(22) PCT Filed: May 23, 2019

(86) PCT No.: PCT/EP2019/063387
§ 371 (c)(1),
(2) Date: Nov. 21, 2020

(87) PCT Pub. No.: WO2019/224330
PCT Pub. Date: Nov. 28, 2019

(65) Prior Publication Data
US 2021/0198166 A1 Jul. 1, 2021

(30) Foreign Application Priority Data

May 23, 2018 (FR) ...................................... 1854284

(51) Int. Cl.
*C07C 6/04* (2006.01)
*B01D 3/14* (2006.01)
(Continued)

(52) U.S. Cl.
CPC ............... *C07C 6/04* (2013.01); *B01D 3/143* (2013.01); *B01D 3/4261* (2013.01);
(Continued)

(58) Field of Classification Search
CPC ........ B01J 23/30; B01J 29/0341; B01J 29/40; B01J 35/0006; B01J 37/0201;
(Continued)

(56) References Cited

U.S. PATENT DOCUMENTS 9,834,497 B2 * 12/2017 Shaikh ...................... C07C 4/06

FOREIGN PATENT DOCUMENTS

| WO | 2005110951 A1 | 11/2005 |
| WO | 2017003818 A1 | 1/2017 |

OTHER PUBLICATIONS

The International Search Report issued in connection with PCT/EP2019/063387 dated Jul. 23, 2019.
(Continued)

*Primary Examiner* — Sharon Pregler
(74) *Attorney, Agent, or Firm* — Locke Lord LLP; Alan B. Clement; Alicia J. Carroll

(57) ABSTRACT

A method for producing a stream of propylene and associated facility are described. The method includes: an introduction of a feed cut rich in C4 and/or C5 hydrocarbons, and at least one cut rich in ethylene into a metathesis reactor; an introduction of a metathesis product in a deethylenizer; a production of an overhead stream rich in ethylene and a feed stream; an introduction of the feed stream into a depropylenizer and recovery of a bottom stream containing C4+ hydrocarbons; a recovery, from an overhead stream of the depropylenizer, of the propylene stream; a lateral withdrawal of a recycle stream and return of the recycle stream to the metathesis reactor; a lateral draw-off, in the depropylenizer, of a purge rich in C4 paraffinic hydrocarbons and/or rich in isobutene.

18 Claims, 3 Drawing Sheets

(51) Int. Cl.
  *B01D 3/42*  (2006.01)
  *B01J 19/24* (2006.01)
  *C07C 4/04*  (2006.01)
  *C07C 4/06*  (2006.01)
  *C07C 7/00*  (2006.01)
  *C07C 7/04*  (2006.01)
(52) U.S. Cl.
  CPC ............... *B01J 19/245* (2013.01); *C07C 4/04* (2013.01); *C07C 4/06* (2013.01); *C07C 7/005* (2013.01); *C07C 7/04* (2013.01); *B01J 2219/0004* (2013.01)
(58) Field of Classification Search
  CPC .. B01J 2219/00033; C07C 11/06; C07C 4/06; C07C 6/04; C07C 2521/08; C07C 2523/30; C07C 2529/40
  See application file for complete search history.

(56) References Cited

OTHER PUBLICATIONS

The Search Report issued in connection with FR 1854284 dated Feb. 22, 2019.

* cited by examiner

METHOD FOR PRODUCING A STREAM OF PROPYLENE AND ASSOCIATED FACILITY

The present invention relates to a method for producing a stream of propylene, comprising the following steps:
- an introduction of a feed cut rich in C4 and/or C5 hydrocarbons, and at least one cut rich in ethylene in a metathesis reactor;
- a recovery of a metathesis product at the outlet of the metathesis reactor;
- an introduction of the metathesis product into a Deethylenizer;
- a production at the head of the Deethylenizer of an overhead stream rich in ethylene and at the bottom of the Deethylenizer of a feed stream;
- an introduction of the feed stream into a Depropylenizer and recovery at the bottom of the Depropylenizer of a bottom stream containing C4+ hydrocarbons;
- a recovery, from an overhead stream of the Depropylenizer, of the propylene stream; and
- a lateral withdrawal of a recycling stream rich in C4 or/and C5 hydrocarbons and return of the recycling stream to the metathesis reactor.

Such a method implemented in particular within or in parallel with a hydrocarbon cracking unit, in particular a steam cracking unit and/or a refinery (FCC catalytic cracking unit, or others).

BACKGROUND

Propylene is produced by the method by contacting a stream of 2-butene and a stream of ethylene in a metathesis reactor.

In a known method, the stream of 2-butene and the stream of ethylene for metathesis come from a steam cracking unit. A C4 refinery cut (catalytic cracking or others) is optionally used as another source of butene. The C4 cut(s) is/are usually treated upstream of the metathesis to obtain a feed which is free of butadiene, poor in isobutene and with a 2-butene/1-butene ratio oriented as much as possible towards 2-butene. 2-Butene may also be obtained by dimerization of ethylene to 1-butene, then by isomerization of 1-butene to 2-butene.

In the case of a C4 steam cracking cut, the cut is typically treated in a unit for the selective hydrogenation of butadiene, also ensuring the hydroisomerization of 1-butene to 2-butene, before being treated in a distillation column to remove isobutene. Alternatively, the butadiene may be extracted using a dedicated unit and/or isobutene is extracted via an MTBE-type unit. The raffinate extracted from this unit(s), rich in 2-butene, is then sent to the metathesis reactor.

A separation section is also provided downstream of the metathesis unit to treat the effluent. A first distillation column (hereinafter referred to as "Deethylenizer") separates the unreacted ethylene from the C3+ cut produced by the metathesis reactor.

The ethylene recovered overhead is separated into an ethylene purge and recycle of ethylene to the metathesis reactor.

The C3+ cut produced at the bottom of the Deethylenizer is sent to a second distillation column (hereinafter referred to as "Depropylenizer"). The propylene is produced at the top of this column. A cut rich in C4 hydrocarbons is withdrawn in liquid phase between the feed plate and the bottom of the column, then is recycled to the metathesis reactor.

Such a method is not optimal in terms of ultimate propylene yield and/or reactor cycle time.

First of all, recycling paraffinic compounds (isobutane, n-butane, . . . ) to the reactor is unnecessary, since these saturated compounds are by nature inert with respect to the metathesis reaction.

Furthermore, the metathesis reaction of isobutene with ethylene does not give new products, while the metathesis reaction of isobutene with itself and/or the other C4 olefinic hydrocarbons is limited in the presence of excess ethylene. It is therefore not advantageous to recycle the isobutene to the metathesis reactor.

When these compounds are present in the unit in large quantities, they block the active sites of the catalyst to little or no yield, and they accumulate in the recycle rich in C4 hydrocarbons. This leads to unnecessary overconsumption and/or to a limitation of the unit, unless it is necessary to provide equipment of greater capacity.

Furthermore, the cut rich in C4 hydrocarbons intended to be recycled to the metathesis reactor is extracted from the Depropylenizer by withdrawing in liquid phase from the bottom zone of the column. This arrangement means that some of the heavy components (in particular C6+ hydrocarbons) formed during the metathesis reaction and/or produced by side reactions are also recycled to the reactor. Such compounds cause fouling and premature coking of the catalyst, which may reduce the cycle time of the catalysts used for the metathesis reaction, and ultimately their life.

SUMMARY OF THE INVENTION

It is an object of the invention to provide a method for the production of very high quality propylene from a metathesis reactor, exhibiting improved yield and/or increased capacity, without significantly affecting the structure of the equipment used for implement the method.

The present invention provides a method for the production of very high quality propylene from a metathesis reactor, comprising the following step:
- lateral draw-off, in the Depropylenizer, of a purge rich in C4 paraffinic hydrocarbons and/or rich in isobutene.

The method according to the invention may comprise one or more of the following characteristics, taken alone or in any technically feasible combination:
- said method comprises recycling the purge rich in C4 paraffinic hydrocarbons and/or rich in isobutene to a steam cracking furnace;
- the overhead stream from the Depropylenizer is at least partially condensed to form a liquid fraction, the liquid fraction being separated into a reflux introduced at a level N1 of the Depropylenizer and into the propylene stream, the purge rich in C4 paraffinic hydrocarbons and/or rich in isobutene being withdrawn from the Depropylenizer laterally at a level N2 located below the level N1;
- the lateral withdrawal of the recycling stream is carried out at a level N4 of the Depropylenizer located below the level N2 of lateral draw-off of the purge rich in C4 paraffinic hydrocarbons and/or rich in isobutene;
- lateral sampling of the recycling stream is carried out in a gas phase;
- the purge rich in C4 paraffinic hydrocarbons and/or rich in isobutene is withdrawn in a gas phase;
- said method according to the aforementioned type comprises the following steps:
 cooling and/or condensation of the recycling stream, introduction of the cooled and/or condensed recycling stream into the feed cut; and the feed cut is formed from a C4 steam cracking cut, or/and a C4 refinery cut advantageously obtained by catalytic cracking.

The present invention also provides a method for producing a stream of propylene, comprising the following steps:
- an introduction of a feed cut rich in C4 and/or C5 hydrocarbons, and at least one cut rich in ethylene in a metathesis reactor;
- a recovery of a metathesis product at the outlet of the metathesis reactor;
- an introduction of the metathesis product into a Deethylenizer;
- a production at the head of the Deethylenizer of an overhead stream rich in ethylene and at the bottom of the Deethylenizer of a feed stream;
- an introduction of the feed stream into a Depropylenizer and recovery at the bottom of the Depropylenizer of a bottom stream containing C4+ hydrocarbons;
- a recovery, from an overhead stream of the Depropylenizer, of the propylene stream;
- a lateral withdrawal of a recycling stream rich in C4 or/and C5 hydrocarbons and return of the recycling stream to the metathesis reactor;

wherein the lateral withdrawal of the recycling stream is carried out in a gas phase.

The method according to the invention does not necessarily comprise lateral draw-off, in the Depropylenizer, of a purge rich in C4 paraffinic hydrocarbons and/or rich in isobutene. It may comprise one or more of the characteristics mentioned above, taken in isolation or in any technically possible combination.

The present invention also provides a propylene production installation, comprising:
- a metathesis reactor supplied with at least one feed cut rich in C4 and/or C5 hydrocarbons, and by at least one cut rich in ethylene, the metathesis reactor producing a metathesis product;
- a Deethylenizer, fed by the metathesis product from the metathesis reactor, the Deethylenizer producing, at the top, an overhead stream rich in ethylene and producing, at the bottom, a feed stream;
- a Depropylenizer receiving the feed stream and producing, at the bottom, a bottom stream containing C4+ hydrocarbons and, at the top, an overhead stream rich in propylene;
- an assembly for recovering, from the head stream of the Depropylenizer, a stream of propylene;
- an assembly for lateral sampling of a recycling stream rich in C4 and/or C5 hydrocarbons and for returning the recycling stream to the metathesis reactor;

wherein:
- a lateral draw-off assembly, in the Depropylenizer, of a purge rich in C4 paraffinic hydrocarbons and/or rich in isobutene.

The installation according to the invention may comprise one or more of the following characteristics, taken in isolation or in any technically feasible combination:
- said installation comprises at least one recycler of the purge rich in C4 paraffinic hydrocarbons and/or rich in isobutene to a steam cracking furnace;
- said installation comprises a condenser suitable for at least partially condensing the overhead stream from the Depropylenizer to form a liquid fraction, and a separator suitable for fractionating the liquid fraction into a reflux introduced at a level N1 of the Depropylenizer and into the stream of propylene, the assembly for withdrawing the purge rich in C4 paraffinic hydrocarbons and/or rich in isobutene being disposed laterally at a level N2 located below the level N1;
- the lateral sampling assembly is suitable for taking a recycling stream rich in C4 hydrocarbons in the gas phase;
- the draw-off assembly is suitable for withdrawing the purge rich in C4 paraffinic hydrocarbons and/or rich in isobutene in the gas phase;
- said installation comprises:
  an assembly for cooling and/or condensation of the recycling stream,
  an assembly for introducing the cooled and/or condensed recycling stream into the feed cut;
- the Depropylenizer comprises an internal partition wall defining a first region located on one side of the separation wall facing a feed inlet of the feed stream and an opposite region located on the other side of the wall for separating from the feed inlet of the feed stream, the lateral draw-off assembly of the purge rich in C4 paraffinic hydrocarbons and/or rich in isobutene opening into the opposite region;
- the Depropylenizer comprises two fractionation columns in series;
- the installation comprises a condenser suitable for at least partially condensing the overhead stream from the Deethylenizer to form a liquid fraction and a vapor purge, and a suitable separator for fractionating the liquid fraction into a reflux introduced into the Deethylenizer and into a stream ethylene recycle returned to the metathesis reactor.

The present invention also provides a propylene production installation, comprising:
- a metathesis reactor supplied with at least one feed cut rich in C4 or/and C5 hydrocarbons, and by at least one cut rich in ethylene, the metathesis reactor producing a metathesis product;
- a Deethylenizer, fed by the metathesis product from the metathesis reactor, the Deethylenizer producing, at the top, an overhead stream rich in ethylene and producing, at the bottom, a feed stream;
- a Depropylenizer receiving the feed stream and producing, at the bottom, a bottom stream containing C4+ hydrocarbons and, at the top, an overhead stream rich in propylene;
- an assembly for recovering, from the head stream of the Depropylenizer, a stream of propylene;
- an assembly for lateral withdrawal of a recycling stream rich in C4 or/and C5 hydrocarbons and returning the recycling stream to the metathesis reactor;

wherein the lateral withdrawal assembly is designed to take a recycle stream in a gas phase.

The installation according to the invention does not necessarily comprise a lateral draw-off assembly, in the Depropylenizer, of a purge rich in C4 paraffinic hydrocarbons and/or rich in isobutene. It may comprise one or more of the characteristics mentioned above, taken alone or in any technically feasible combination.

BRIEF DESCRIPTION OF THE DRAWINGS

The invention will be better understood upon reading the description which follows, given solely by way of example, and made with reference to the accompanying drawings, in which.

DETAILED DESCRIPTION

In what follows, the same reference designates a fluid circulating in a pipe and the pipe which transports this fluid. Furthermore, unless otherwise indicated, the percentages are molar percentages and the pressures are in relative bars.

Figure 1:
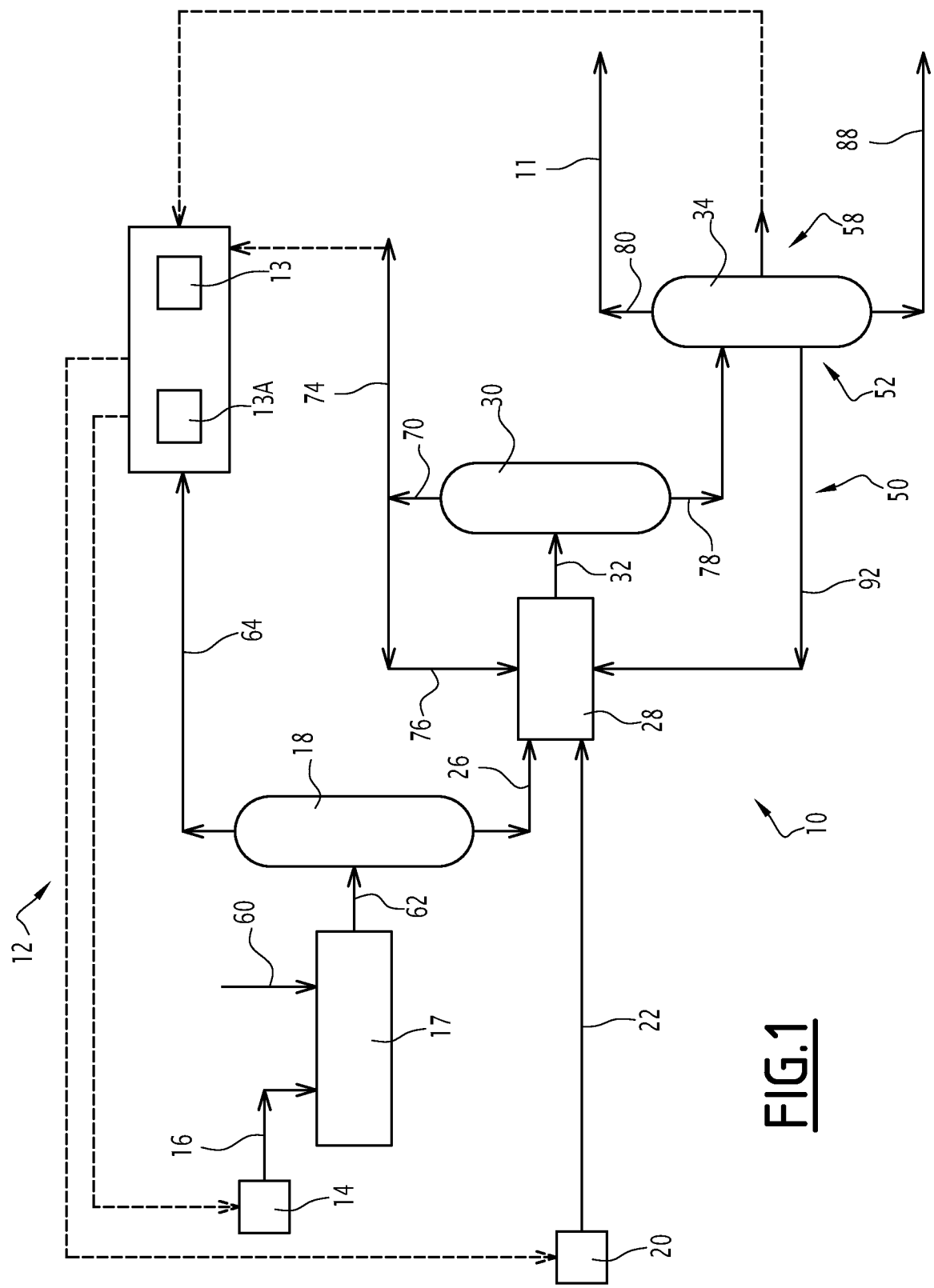
FIG. 1 is a functional block diagram of a first production installation for implementing a method according to the invention.
Figure 2:
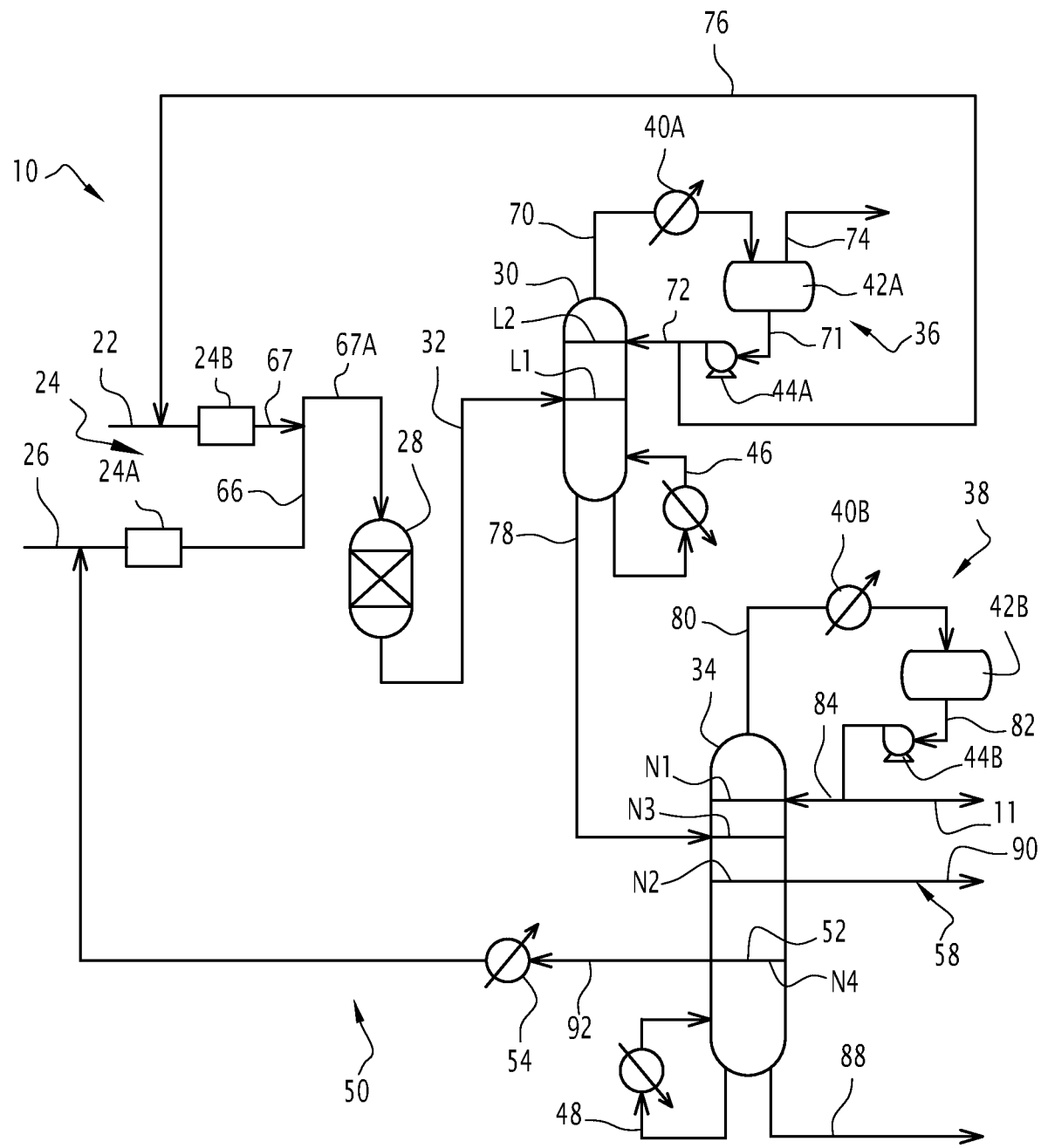
FIG. 2 is a detailed view of the metathesis unit of the installation of FIG. 1.

A first installation 10 for producing a stream 11 of propylene is illustrated in FIGS. 1 and 2. The installation 10 is integrated within a unit 12 for the production of hydrocarbon derivatives, in particular within a hydrocarbons cracking and separation unit, partially illustrated in FIG. 1.

The unit for the production of hydrocarbon derivatives 12 comprises at least one steam cracker 13 and/or a refining unit 13 of the catalytic cracker or other type, and distillation columns 13A, suitable for successively separating cuts of hydrocarbons.

In particular, the unit for the production of hydrocarbon derivatives 12 comprises equipment 14 for producing a raw cut 16 of C4 hydrocarbons, equipment 17 for the selective hydrogenation of the butadiene contained in the raw cut 16, also ensuring hydroisomerization of 1-butene to 2-butene from cut 16, and a column 18 for separating isobutene.

The equipment 17 and 18 may respectively be replaced by butadiene extraction units followed by 1-butene to 2-butene isomerization (block 17) and by a methyl tert-butyl ether MTBE unit (block 18).

The unit for the production of hydrocarbon derivatives 12 further comprises equipment 20 for the production of a cut 22 rich in ethylene.

With reference to FIG. 2, the installation 10 comprises at least one piece of equipment 24 for purifying the cut rich in ethylene 22 and for purifying a feed cut 26 rich in C4 olefinic hydrocarbons coming from the separation column 18. The installation 10 further comprises a metathesis reactor 28, a first separation column (hereinafter referred to as "Deethylenizer 30"), for the separation of a metathesis product 32 produced in the reactor 28 and a second separation column (hereinafter referred to as "Depropylenizer 34") for the separation of an effluent from Deethylenizer 30.

Deethylenizer 30 and Depropylenizer 34 are each provided with a condensation and reflux system respectively 36 and 38 each comprising a condenser respectively 40A, 40B, a separator respectively 42A, 42B and a reflux pump respectively 44A, 44B.

Deethylenizer 30 and Depropylenizer 34 are also each provided with a bottom reboiler 46 and 48 respectively.

The installation 10 further comprises a recycling circuit 50 for a stream rich in C4 hydrocarbons comprising a withdrawal assembly 52 in the Depropylenizer 34, and a heat exchanger 54 for cooling the stream rich in C4 hydrocarbons.

The installation 10 further comprises in this example a lateral draw-off assembly 58, in the Depropylenizer 34, of a stream rich in C4 paraffinic hydrocarbons and/or rich in isobutene. The lateral draw-off assembly 58 has at least one side drain in the Depropylenizer 34.

A method for producing propylene in the installation 10 will now be described.

Initially, the raw cut 16 of C4 hydrocarbons is produced from the steam cracker 13 and/or from a refining unit 13 (catalytic cracker or others), and from separation steps in the equipment 14.

In the case where this cut 16 is produced only by a steam cracker, and advantageously when the latter is operated at a medium severity (for example P/E=0.61), the C4 cut contains traces of acetylenic C4 compounds (for example less than 5 mol %), between 40 mol % and 50 mol % of butadiene (in particular approximately 45 mol %), between 15 mol % and 25 mol % of 1-butene (in particular approximately 19 mol %), between 5 mol % and 15 mol % of 2-butene (in particular approximately 10 mol %), between 15 mol % and 25 mol % of isobutene (in particular approximately 20 mol %) and between 2 mol % and 10 mol % of C4 paraffinic compounds (in particular approximately 6 mol % of n-butane and isobutane).

The compounds for a cut from a refinery (FCC or others) is similar except for the percentage of paraffinic compounds which is greater, for example greater than 11 mol %.

Typically, cut 16 is first introduced into the equipment 17 to remove butadiene by selective hydrogenation also providing hydroisomerization of 1-butene to 2-butene. Thus, cut 16 is contacted with a stream of hydrogen 60 and a hydrogenated stream 62 of C4 hydrocarbons containing 1-butene, 2-butene, isobutene and C4 paraffins is produced. Alternatively, cut 62 is produced by extracting butadiene.

The hydrogenated stream 62, free of butadiene, may then be treated in several ways to produce a stream depleted in isobutene, for example by means of the isobutene separation column 18.

In this case, column 18 produces an overhead stream 64 which contains the separated isobutene, the isobutane from the hydrogenated stream 62 and part of the 1-butene, since the 1-butene has a boiling point very close to isobutene (less than 1° C. difference at atmospheric pressure between the boiling point of isobutene and the boiling point of 1-butene).

Column 18 produces at the bottom a stream constituting the feed section 26.

The feed cut 26 mainly contains (e.g. more than 60 mol %) normal olefins, normal paraffins and, in small amounts (e.g. less than 20 mol %) iso-olefins and iso-paraffins.

Alternatively, isobutene may also be removed by different reactions which comprise reaction with methanol to form MTBE, reaction with water to form tert-butyl alcohol (TBA) or reaction with itself to form a C8 stream.

The feed cut 26, in the case of production from a C4 steam cracker stream (operated advantageously at a typical P/E of 0.61) treated by hydrogenation then fractionation to remove the isobutene, has a lot of 2-butene (for example of the order of 80 mol % or more). As an embodiment according to the different treatments explained above and/or the origin of the C4 cut, the 2-butene composition is smaller.

In other embodiments, the C4 cut is mixed (or even replaced) with a C5 hydrocarbon cut.

The feed cut 26 is rich in C4 and/or C5 olefinic hydrocarbons, the content of C4 and/or C5 olefinic hydrocarbons in the feed cut 26 being generally greater than 65 mol %.

The following description relates to a feed cut 26 made up of C4 hydrocarbons, but the same developments may be extrapolated to a feed cut 26 made up of a mixture of C4 and C5 hydrocarbons, or even to a cut of C4 and C5 hydrocarbons or a feed cut 26 consisting of C5 hydrocarbons only.

In parallel, the ethylene-rich cut 22 is produced, for example, from the steam cracker 13 and from separation steps in the equipment 20.

The ethylene-rich cut 22, when produced from a steam cracker typically has an ethylene molar content of greater than 99.9%. However, the method does not require such a high purity and ethylene having a chemical grade (lower contents i.e. 99 mol % or less) is also acceptable.

Then, the feed cut 26 and the ethylene-rich cut 22 are processed in the equipment 24 in order to ensure the capture of the poisons of the metathesis catalyst such as water, sulfur, alcohols, CO2, nitrogen compounds, heavy metals.

Depending on the source of the loads and their battery limit conditions, the equipment 24A, 24B is dedicated or combined guard beds. Usually, they also process the ethylene recycle stream 76 and the recycle stream 92 rich in C4 hydrocarbons which will be described below.

In the example shown in FIG. 2, the guard beds 24A, 24B are dedicated. The feed cut 26 (and associated recycle stream 92) is processed on a liquid phase bed 24A to form a processed feed cut 66 and the ethylene rich cut 22 (and associated recycle stream 76) is processed on a bed 24B in vapor phase to form a cut rich in processed ethylene 67.

The processed feed cut 66 is then mixed with the processed ethylene-rich cut 67. The mixture forms a feed cut 67A for the reactor 28 which is vaporized, heated and introduced into the metathesis reactor 28.

In one embodiment (not shown), the cut 26 and the cut 22 (as well as the respective streams 92 and 76) are mixed and introduced into the same guard bed 24A operating in the liquid phase, to form the cut 67A for feeding the reactor 28. Cut 67A is sent to metathesis reactor 28 after vaporization and reheating.

In a known manner, a metathesis reaction between 2-butene and ethylene occurs in metathesis reactor 28, due to the presence of a catalyst. This causes fragments to interchange between 2-butene and ethylene molecules to form propylene molecules as the main reaction. A metathesis reaction may theoretically occur between any olefinic compound, since it is the inversion of alkyl groups around double bonds. Many side reactions therefore take place in the reactor. All of these reactions are governed by the laws of equilibrium.

In order to promote equilibrium towards the main reaction, the flow rate of the ethylene-rich cut 22 is optimized so as to work in excess of ethylene. Thus the ratio of the molar flow rates of ethylene and of butene (1-butene and 2-butene) in the 67 A reactor feed cut is advantageously between 1.3 and 3.

The metathesis reaction takes place at a temperature generally between 250° C. and 380° C., and at a pressure between 20 bar and 35 bar.

The catalyst used generally comprises a combination of a catalyst dedicated to metathesis (a transition metal optionally combined with an oxide, for example tungsten oxide supported on silica or rhenium oxide supported on alumina) and a catalyst dedicated to isomerization (an oxide of a metal from group II of the periodic table of the elements, for example magnesium oxide or calcium oxide).

A metathesis product 32 is formed at the outlet of the metathesis reactor 28.

Metathesis product 32 comprises ethylene, propylene, C4 olefinic hydrocarbons including unreacted 1-butene and 2-butene, heavier olefinic compounds and paraffinic hydrocarbons.

The metathesis product 32 is then introduced into the Deethylenizer 30 at a first intermediate level of supply L1.

The pressure prevailing in the Deethylenizer 30 is usually between 18 bars and 30 bars. Deethylenizer 30 is a cryogenic column. The condenser 40A typically uses C3 hydrocarbons as the coolant.

An overhead stream 70 is produced at the top of the Deethylenizer 30. Overhead stream 70 typically contains an ethylene content greater than 95 mol %. The overhead stream 70 is at least partially condensed in the condenser 40A, then is fed into the separator 42A.

In separator 42A, the partially condensed overhead stream 70 is separated into a liquid stream 71 and a vapor purge 74.

The liquid stream 71 recovered in the flask 42 is typically pumped and separated into a reflux 72 and an ethylene recycle stream 76. The vapor purge 74 aims to deconcentrate the ethylene recycle stream 76 from light compounds which may accumulate (methane, ethane, etc.).

The ethylene recovered in the recycle stream 76 usually corresponds to more than 95% of the ethylene contained in the metathesis product 32.

The reflux 72 is introduced at a level L2 of the Deethylenizer 30, the level L2 being located above the supply level L1.

The ethylene recycle stream 76 is recycled to the metathesis reactor 28. In the example illustrated in FIG. 2, the stream 76 is mixed with the ethylene-rich cut 22, upstream of the treatment assembly 24.

A feed stream 78 for feeding the Depropylenizer 34 is produced at the bottom of Deethylenizer 30.

This feed stream 78 contains propylene, typically about 99% of the propylene contained in the metathesis product 32, as well as the C4 hydrocarbons which have not been converted in the metathesis reactor 28 and heavier C5+ hydrocarbons resulting from secondary metathesis reactions and/or already present in the feed cut 26.

The ethylene content is almost zero (for example less than 20 ppm by volume by volume) since it must be compatible with the ethylene specification of the propylene stream 11 which is typically very low (less than 40 ppm by volume, in particular 30 ppm by volume approximately).

The feed stream 78 is introduced into the Depropylenizer 34 at a feed level N3.

The pressure prevailing in the Depropylenizer 34 is usually between 15 bars and 25 bars.

Depropylenizer 34 produces an overhead stream 80 which is very high purity propylene. Advantageously, the overhead stream 80 has a specification typical of the propylene grade polymer, greater than 99.6% by volume, or even greater than 99.9% by volume.

Overhead stream 80 is at least partially condensed, usually using water as a cold fluid, in condenser 40B, and then is introduced into separator 42B. A liquid fraction 82 is taken from the bottom of separator 42B, then is pumped into pump 44B, before being separated into reflux 84, and into propylene stream 11. The reflux 84 is reintroduced into the Depropylenizer 34 at a level N1 located above the level N3.

As indicated above, the propylene stream 11 has a "polymer quality", with a molar propylene content generally greater than 99.6% by volume, or even greater than 99.9% by volume, an ethylene content generally less than 50 ppm by volume, typically of the order of 30 ppm by volume and a C4 hydrocarbon content generally less than 40 ppm by volume, typically of the order of 20 ppm by volume.

The propylene recovered in stream 11 usually corresponds to more than 99.5% of the propylene contained in feed stream 78.

A withdrawal from a recycling stream 92 rich in C4 hydrocarbons, containing the majority (advantageously more than 70%) of the n-butene compounds of the metathesis product 32 which have not been converted in the metathesis reactor 28, is taken from the Depropylenizer 34 via the withdrawal assembly 52, at a level N4 located below the supply level N3.

Usually, this recycle stream 92 also contains part of the C5 hydrocarbons produced in the metathesis reactor 28 and/or present in the feed cut 26.

The recycle stream 92 is recycled to the metathesis reactor 28. Thus, it is cooled in the exchanger 54 before being reintroduced into the feed cut 26 upstream of the purification equipment 24.

Advantageously, the amount of olefinic C5 in the recycle stream 92 is optimized so as to limit, or even block, certain side reactions in the metathesis reactor 28.

A bottom stream 88 is taken from the bottom of the Depropylenizer 34. The bottom stream 88 purges the C6 and heavier hydrocarbons, as well as the C4 and C5 hydrocarbons which cannot react by metathesis.

The purge rate is typically set to contain enough paraffinic C4 to prevent their accumulation in recycle stream 92. Alternatively, Depropylenizer 34 is followed by another distillation column (not shown) receiving the bottom stream 88 so as to separate compounds C4 and C5+.

According to certain embodiments of the invention, a purge 90 rich in paraffinic hydrocarbons C4 and/or rich in isobutene is withdrawn from the Depropylenizer 34 via the lateral draw-off assembly 58, at a withdrawal level N2 located below the supply level. N3, and located above the level N4 for withdrawal of the recycling stream 92.

Purge 90 contains light, non-reactive components such as C4 paraffinic hydrocarbons, particularly isobutane and n-butane. It also contains some light olefins which are unattractive to the method, in particular isobutene.

The amount of C4 paraffinic hydrocarbons and/or isobutene in purge 90 is generally greater than 50 mol %, in particular greater than 60 mol %.

Since the boiling points of the C4 hydrocarbons are very close, purge 90 also contains 1-butene and 2-butene. The position of this draw-off in Depropylenizer 34 and the flow rate extracted from Depropylenizer 34 are optimized to minimize the entrainment of these latter two compounds.

The molar flow rate ratio between purge 90 and feed stream 78 is therefore adjusted depending on the amount of n-butane, isobutane, and isobutene present in feed stream 26. A purge of the order of 90% of the C4 paraffinic hydrocarbons present in the feed cut 26, is carried out thanks to the establishment of the purge 90.

The purge 90 is advantageously returned to the steam cracker 13 and/or to the catalytic cracker 13. Thus, the paraffinic hydrocarbons present in the purge 90 are used to produce additional olefins which are separated upstream from the installation 10.

The ultimate yield of the method for producing propylene by metathesis is generally defined by:

$$\text{Ultimate yield} = \frac{\text{Propylene}_{produced}/2}{(1\text{-butene} + 2\text{-butene})_{fresh\ load\ (cut\ 26)}} \text{ in mol}$$

The conversion of the metathesis reactor 28 is defined by:

$$(1\text{-butene} + 2\text{-butene})_{reacter\ inlet} -$$

-continued $$\text{Conversion} = \frac{(1\text{-butene} + 2\text{-butene})_{reacter\ outlet}}{(1\text{-butene} + 2\text{-butene})_{reacter\ inlet}}$$

The theoretical maximum conversion is very dependent on the load since it is dictated by the equilibrium of all the metathesis reactions involved. In all cases the expected values are of the order of 70% maximum, or even less if the cut 26 is rich in 1-butene. It is therefore essential to obtain attractive ultimate yields (for example of the order of 80% to 90%) to recycle unreacted 1-butene and 2-butene to metathesis reactor 28. Thus, at a constant flow rate of the recycling stream 92 rich in C4 hydrocarbons:

the more this stream 92 will be rich in 1-butene and 2-butene, the better the ultimate yield will be; Conversely the more this stream 92 will contain inert vis-à-vis the metathesis reaction (typically paraffins) and/or compounds capable of limiting the main reaction from 2-butene to propylene (typically isobutene), the less good will be the ultimate yield.

It is therefore also induced that at constant ultimate efficiency:

the richer the recycling stream 92 in 1-butene and 2-butene, the smaller the flow rate required; Conversely the more the recycling stream 92 will contain inert relative to the metathesis reaction (typically paraffins) and/or compounds capable of limiting the main reaction from 2-butene to propylene (typically isobutene), the greater the flow rate required.

According to the invention, the draw-off of a purge 90 rich in C4 paraffinic hydrocarbons and/or rich in isobutene reduces the flow rate of the recycling stream 92. Thus, the dimensions of the equipment (and lines) used for recycling are reduced by significantly. Likewise, the total flow rate passing through the purification equipment 24 (for example the guard beds 24A, 24B), in the metathesis reactor 28, in the Deethylenizer 30 and in the Depropylenizer 34 are reduced.

Further, it is not necessary to severely limit the isobutene content in the feed cut 26 of the metathesis reactor 28, since the isobutene is removed through the purge 90. This results in energy savings and high performance, reduction in the size of the pre-processing equipment, in particular of the isobutenes separation column 18.

Finally, the method according to the invention offers a possibility of de-bottlenecking the installation 10. In fact, as seen above, the addition of a purge 90 rich in C4 paraffinic hydrocarbons and/or rich in isobutene, provides the opportunity to operate the installation 10 with a limited C4 hydrocarbon recycling stream 92, and/or to improve the ultimate yield at the same recycling rate 92. This advantage increases the production of propylene, by increasing the stream of the feed cut 26 without having to modify the existing equipment significantly.

The recycling stream 92 is withdrawn in liquid form. In one embodiment, the recycling stream 92 rich in C4 hydrocarbons is advantageously withdrawn in a gas phase. Thus, compared to a liquid withdrawal, the quantity of heavy components in the recycling stream 92 is greatly reduced, in particular that of C6+ hydrocarbons.

By way of illustration, the recoveries in the Depropylenizer 34 of the various compounds present in the recycle stream 92 obtained from a feed cut 26 as described in Table 1 below are illustrated in Table 2 below. The definition of the recovery R of compound X in Depropylenizer 34 is understood as:

$$R = \frac{(X)_{Recycling\ (stream\ 92)}}{(X)_{inlet\ 34\ (stream\ 78)}} \times 100$$

$(X)$ = flow rate of compound X

Table 2 compares an installation of the prior art, devoid of purge 90 of C4 paraffinic hydrocarbons, with an installation 10 according to the invention. Two hypotheses are presented for the draw-off of the purge 90 according to the invention (liquid withdrawal or gas withdrawal).

The embodiment in which the recycle stream 92 is gaseous is also presented in Table 2.

The feed cut 26 has the following composition:

TABLE 1

| Composition of the feed cut 26 (% mol) | |
| --- | --- |
| Propylene | 0.6 |
| Isobutene | 2.1 |
| 1-butene | 5.3 |
| 2-butene | 59.6 |
| n-butane | 26.0 |
| Isobutane | 5.4 |
| Pentenes | 1.0 |

The data for the different options in Table 2 all consider the same mass flow rate of the recycling stream 92 of C4 hydrocarbons (typically the mass flow rate of the recycling stream 92 and considered identical to the mass flow rate of the feed cut 26) and the same excess ethylene in the metathesis reactor 28.

TABLE 2

| | Recovery in the Depropylenizer 34 according to the invention (with purge 90) | | |
| --- | --- | --- | --- |
| Recovery in the Depropylenizer 34 according to the prior art (without purge 90) | Purge 90 liquid | Purge 90 gas | P Purge 90 gas + recycling stream 92 gas withdrawn |
| Isobutane 79% | 74% | 71% | 53% |
| Isobutene 76% | 74% | 72% | 61% |
| 1-butene 75% | 73% | 72% | 63% |
| n-butane 66% | 69% | 70% | 72% |
| 2-butene 65% | 68% | 69% | 73% |
| Pentenes 34% | 36% | 36% | 40% |
| C6+ 26% | 25% | 25% | 9% |

Thanks to the implementation of the purge 90, the amount of 2-butene recovered in the recycle stream 92 is significantly greater, allowing better reuse of this compound and therefore a better ultimate yield of propylene.

Conversely, the quantity of light paraffinic compounds inert with respect to the metathesis reaction (in particular, isobutane) and of light compounds capable of limiting the main reaction of 2-butene towards propylene (in particular isobutene) is significantly reduced, avoiding unnecessary recycling of these compounds to the reactor.

In the example presented, the gains are even more attractive when the purge 90 is withdrawn in gas form rather than liquid form and when the C4 hydrocarbon recycle stream 92 is itself withdrawn in gas rather than liquid form.

In addition, the recovery of C6+ hydrocarbons in the Depropylenizer goes from a typical value of around 25% when the withdrawal from recycle stream 92 is liquid to less than 10% when it is gas. This sharp decrease in the recovery of C6+ hydrocarbons when the recycle stream 92 passes from liquid to vapor is independent of the presence of the purge 90 rich in C4 paraffinic hydrocarbons and/or rich in isobutene.

When the recycle stream 92 is withdrawn in the vapor phase, the heavy compounds which are sources of fouling and premature coking of the metathesis catalyst are almost no longer recycled to the reactor 28, which extends the cycle time of the catalyst. As successive regenerations at very high temperature decrease the activity of the catalyst, the catalyst must be replaced after a few cycles. An extension of the cycle time therefore lengthens the life of the catalysts.

The yields expected from the implementation of the purge 90 rich in C4 paraffinic hydrocarbons and/or rich in isobutene depend on the composition of the feed cut 26. In the example presented above (feed cut 26 according to Table 1):

at the same flow rate of the recycling stream 92 of the cut rich in C4 hydrocarbons, the ultimate yield is increased by 1.5%;

at the same production of propylene, the flow rate of the recycling stream 92 of the cut rich in C4 hydrocarbons is reduced by approximately 15%, which reduces the size of the purification equipment 24, of the metathesis reactor 28, of the Deethylenizer 30 and Depropylenizer 34 of the order of 6%.

The choice between a purge 90 in gas or liquid form is a compromise between an increase in production and capital investment expenses (CAPEX) since the final destination of the purge 90 must also be taken into account.

Figure 3:
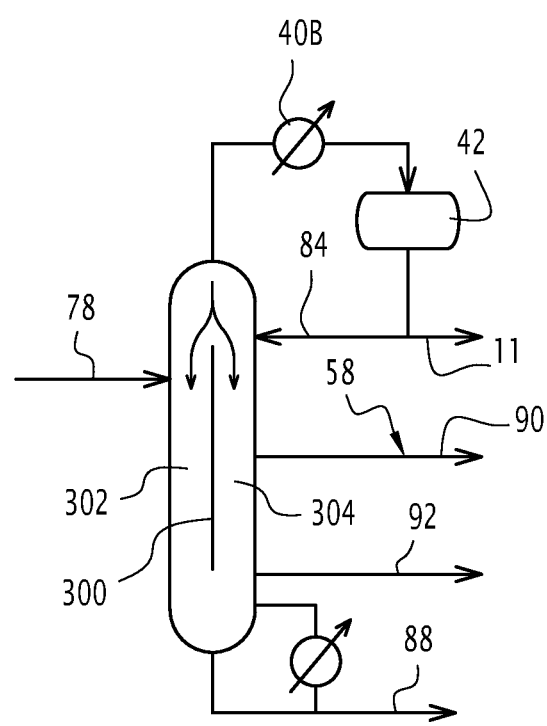
FIG. 3 is a detail view of a second production installation for implementing a method according to the invention.

In an embodiment illustrated in FIG. 3, the installation 10 according to the invention still comprises a purge 90 of paraffinic hydrocarbons, C4 and/or rich in isobutene. The recycling stream 92 rich in C4 hydrocarbons is taken in liquid form from the Depropylenizer 34.

Depropylenizer 34 then comprises a distillation column arranged according to the concept of divided streams with a vertical internal separation wall 300, visible in FIG. 3. The separation wall 300 defines in the distillation column, a first region 302 located at a side of the partition wall 300 facing the feed inlet of the feed stream 78 (left in FIG. 3) and an opposing region 304 located on the other side of the partition wall 300 from the feed inlet of the feed stream 78 (on the right in FIG. 3).

Thus, the heaviest compounds (in particular the C6+ hydrocarbons) of the feed stream 78, pass directly through the bottom of the distillation column, via the first region 302 (on the left in FIG. 3) and are discharged into the bottom stream 88.

The light compounds distill in the upper part of the same side of the partition wall 300. The propylene is extracted at the top in the stream 11 and the C4-C5 hydrocarbons continue their separation in the second region 304 defined by the partition wall 300. (on the right in FIG. 3).

The purge 90 rich in C4 paraffinic hydrocarbons and/or rich in isobutene is withdrawn (in gas or liquid form) in the second region 304 defined by the separation wall 300 and the recycle stream 92 rich in C4 hydrocarbons is withdrawn below.

The stream 92 is advantageously withdrawn in the liquid phase, while ensuring a low recovery of the heavy compounds, since the latter are not present at this point in the Depropylenizer 34. The use of the divided stream column as a Depropylenizer 34 extends the processing times cycle of the metathesis reactor 28, following the same principles as those set out above for the Depropylenizer 34 of FIG. 2 with withdrawal of the recycle stream 92 in gaseous form.

In one embodiment, the method is implemented with a lateral withdrawal of the recycle stream 92 rich in C4 and/or C5 hydrocarbons carried out in the gas phase, but without purging 90 of C4 paraffinic hydrocarbons and/or rich in isobutene.

The invention claimed is:

1. A method for producing a stream of propylene, comprising:
    introducing a feed cut rich in C4 and/or C5 hydrocarbons, and at least one cut rich in ethylene into a metathesis reactor;
    recovering a metathesis product at an outlet of the metathesis reactor;
    introducing the metathesis product into a deethylenizer;
    producing, an overhead stream rich in ethylene at a head of the deethylenizer and producing a feed stream at a bottom of the deethylenizer;
    introducing the feed stream in a depropylenizer and recovering a bottom stream containing C4+ hydrocarbons from a bottom of the depropylenizer;
    recovering a propylene stream from an overhead stream of the depropylenizer;
    withdrawing a recycle stream rich in C4 and/or C5 hydrocarbons laterally in the depropylenizer;
    returning the recycle stream to the metathesis reactor;
    drawing-off a purge rich in C4 paraffinic hydrocarbons and/or rich in isobutene, laterally in the depropylenizer,
    wherein the withdrawing the recycle stream is carried out at a level N4 of the depropylenizer, the drawing-off of the purge rich in C4 paraffinic hydrocarbons and/or rich in isobutene being carried out at a level N2 of the depropylenizer, the level N4 being located below the level N2.

2. The method according to claim 1, comprising recycling the purge rich in C4 paraffinic hydrocarbons and/or rich in isobutene to a steam cracking furnace.

3. The method according to claim 1, comprising at least partially condensing the overhead stream from the depropylenizer to form a liquid fraction, separating the liquid fraction in a reflux introduced at a level N1 of the depropylenizer and in the propylene stream, the purge rich in C4 paraffinic hydrocarbons and/or rich in isobutene being drawn off from the depropylenizer laterally at a level N2 located below the level Ni.

4. The method according to claim 1, wherein the withdrawing of the recycle stream is carried out in gas phase.

5. The method according to claim 1, wherein the drawing-off of the purge rich in C4 paraffinic hydrocarbons and/or rich in isobutene is carried out in gas phase.

6. The method according to claim 1, comprising:
    cooling and/or condensing the recycle stream to form a cooled and/or condensed recycle stream,
    introducing the cooled and/or condensed recycle stream into the feed cut.

7. The method according to claim 1, comprising forming the feed cut from a C4 steam cracking cut, and/or a C4 refinery cut.

8. A propylene production installation, comprising:
    a metathesis reactor configured to be supplied with at least one feed cut rich in C4 and/or C5 hydrocarbons, and by at least one cut rich in ethylene, the metathesis reactor being configured to produce a metathesis product;
    a deethylenizer, fed with the metathesis product from the metathesis reactor, the deethylenizer having a deethylenizer top and a deethylenizer bottom, the deethylenizer being configured to produce an overhead stream rich in ethylene at the deethylenizer top, and to produce a feed stream at the deethylenizer bottom;
    a depropylenizer having a depropylenizer top and a depropylenizer bottom, the depropylenizer being configured to receive the feed stream and to produce a bottom stream containing C4+ hydrocarbons at the depropylenizer bottom and to produce an overhead stream rich in propylene at the depropylenizer top;
    a collector configured to collect a propylene stream from the overhead stream of the depropylenizer;
    a lateral withdrawer configured to withdraw a recycle stream rich in C4 and/or C5 hydrocarbons in the depropylenizer and a recycler configured to return the recycle stream to the metathesis reactor;
    a lateral off-drawer configured to draw off a purge rich in C4 paraffinic hydrocarbons and/or rich in isobutene in the depropylenizer,
    wherein the depropylenizer has a level N4 at which the recycle stream is withdrawn, and a level N2 at which the purge rich in C4 paraffinic hydrocarbons and/or rich in isobutene is withdrawn, the level N4 being located below the level N2.

9. The installation according to claim 8, comprising a steam cracking furnace, the recycler being configured to return the purge rich in C4 paraffinic hydrocarbons and/or rich in isobutene to the steam cracking furnace.

10. The installation according to claim 8, comprising a condenser configured to at least partially condense the overhead stream from the depropylenizer to form a liquid fraction, and a separator configured to fractionate the liquid fraction into a reflux introduced at a level N1 of the depropylenizer and into the propylene stream, the lateral off-drawer being disposed laterally at a level N2 located below the level Ni.

11. The installation according to claim 8, wherein the lateral withdrawer is configured to withdraw the recycle stream rich in C4 hydrocarbons in gas phase.

12. The installation according to claim 8, wherein the lateral off-drawer is configured to draw off the purge rich in C4 paraffinic hydrocarbons and/or rich in isobutene in gas phase.

13. The installation according to claim 8, comprising:
    a cooler and/or condenser configured to cool and/or condense the recycle stream to form a cooled and/or condensed recycle stream,
    an introducer configured to introduce the cooled and/or condensed recycle stream in the feed cut.

14. The installation according to claim 8, wherein the depropylenizer comprises an internal partition wall defining a first region located on one side of the partition wall facing a feed inlet of the feed stream and an second opposite region located on the other side of the partition wall from the feed inlet of the feed stream, the lateral off-drawer opening into the second region.

15. The installation according to claim 8, wherein the depropylenizer comprises two fractionation columns in series.

16. The method according to claim 7, comprising obtaining the C4 steam cracking cut, and/or the C4 refinery cut by catalytic cracking.

17. A method for producing a stream of propylene, comprising:

introducing a feed cut rich in C4 and/or C5 hydrocarbons, and at least one cut rich in ethylene into a metathesis reactor;

recovering a metathesis product at an outlet of the metathesis reactor;

introducing the metathesis product into a deethylenizer;

producing an overhead stream rich in ethylene at a head of the deethylenizer and producing a feed stream at a bottom of the deethylenizer;

introducing the feed stream in a depropylenizer and recovering a bottom stream containing C4+ hydrocarbons from a bottom of the depropylenizer;

recovering a propylene stream from an overhead stream of the depropylenizer;

withdrawing a recycle stream rich in C4 and/or C5 hydrocarbons laterally in the depropylenizer;

returning the recycle stream to the metathesis reactor;

the lateral withdrawing of the recycling stream being carried out in gas phase.

18. A method for producing a stream of propylene, comprising:

introducing a feed cut rich in C4 and/or C5 hydrocarbons, and at least one cut rich in ethylene into a metathesis reactor;

recovering a metathesis product at an outlet of the metathesis reactor;

introducing the metathesis product into a deethylenizer;

producing, an overhead stream rich in ethylene at a head of the deethylenizer and producing a feed stream at a bottom of the deethylenizer;

introducing the feed stream in a depropylenizer and recovering a bottom stream containing C4+ hydrocarbons from a bottom of the depropylenizer;

recovering a propylene stream from an overhead stream of the depropylenizer;

withdrawing a recycle stream rich in C4 and/or C5 hydrocarbons laterally in the depropylenizer;

returning the recycle stream to the metathesis reactor;

drawing-off a purge rich in C4 paraffinic hydrocarbons and/or rich in isobutene, laterally in the depropylenizer, wherein an of amount of C4 paraffinic hydrocarbons and/or isobutene in purge is greater than 50 mol %.

* * * * *